United States Patent [19]
van der Burg

[11] 3,965,114
[45] June 22, 1976

[54] IMIDAZOLIDINE DERIVATIVES

[75] Inventor: Willem Jacob van der Burg, Heesch, Netherlands

[73] Assignee: Akzona Incorporated, Asheville, N.C.

[22] Filed: Sept. 4, 1974

[21] Appl. No.: 503,124

[30] Foreign Application Priority Data
Sept. 20, 1973 Netherlands.................... 7312944

[52] U.S. Cl. ............................. 260/309.7; 424/273
[51] Int. Cl.² ......................................... C07D 49/34
[58] Field of Search ................................ 260/309.7

[56] References Cited
UNITED STATES PATENTS
3,127,266   3/1964   Sus et al. ................ 260/309.7 X OTHER PUBLICATIONS
Chem. Abstracts 1961: 15452h.
Chem. Abstracts, 1968, 68:39687h.
Chem. Abstracts, 1960, 21057b.
Chem. Abstracts, 1962, 56:2312g.

Primary Examiner—Ethel G. Love
Attorney, Agent, or Firm—Francis W. Young; Philip M. Pippenger; Hugo E. Weisberger

[57] ABSTRACT

The invention relates to novel imidazolidine derivatives of the general formula:

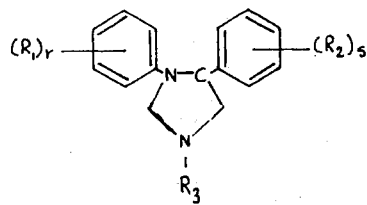

in which
r and s = 0–5,
$R_1$ and $R_2$ = hydroxy, halogen, alkyl or alkoxy with 1–6 carbon atoms, acyloxy with 1–8 carbon atoms or a trifluoromethyl group, $R_3$ = hydrogen, and alkyl group with 1–6 carbon atoms, an aryl group or an aralkyl group (7–9 C)
as well as pharmaceutically acceptable salts thereof, having valuable anticholinergic and anticonvulsive activities.

2 Claims, No Drawings

IMIDAZOLIDINE DERIVATIVES

The invention relates to novel imidazolidine derivatives and to processes for the preparation of these derivatives.

More particularly the invention relates to novel imidazolidine derivatives of the general formula:

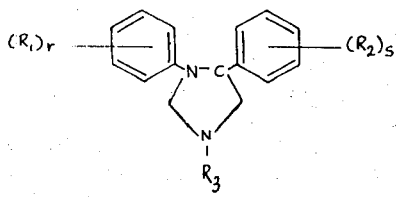

I in which
r and s = 0–5,
$R_1$ and $R_2$ = hydroxy, halogen, alkyl or alkoxy with 1–6 carbon atoms, acyloxy with 1–8 carbon atoms or a trifluoromethyl group,
$R_3$ = hydrogen, an alkyl group with 1–6 carbon atoms, an aryl group or an aralkyl group (7–9 C) as well as pharmaceutically acceptable salts thereof.

In the literature biologically active compounds have been described, differing from the present compounds I in that they possess a piperazine instead of an imidazolidine ring. These known piperazine-compounds possess antihistamine, antiserotonine, cardiovascular and vasodilating activities.

Surprisingly it has now been found that the present imidazolidine derivatives of the formula I do not show antihistamine, antiserotonine, cardiovascular or vasodilating activities at all, but possess valuable anticholinergic and anticonvulsive activities.

The compounds according to the invention can be prepared by any method commonly used for this type of compounds. Most conveniently they are prepared by reacting a starting compound of the general formula II:

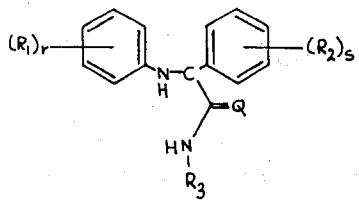

II or an acid addition salt thereof, in which Q = hydrogen ($H_2$) or oxygen and r, s, $R_1$, $R_2$ and $R_3$ have the meaning indicated above, with a reagent of the general formula:

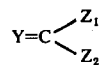

III in which Y = hydrogen ($H_2$), oxygen or sulphur and $Z_1$ and $Z_2$ represent equal or different reactive or "leaving" groups or together represent a bivalent reactive group, which groups can be eliminated together with the hydrogen atom of either nitrogen atom of the diamine II.

In this way a compound is obtained of the general formula:

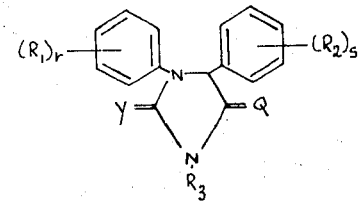

IV or an acid addition salt thereof, in which r, s, $R_1$, $R_2$, $R_3$, Y and Q have the meaning indicated above.

In general the groups $Z_1$ and $Z_2$ may represent halogen, a substituted or unsubstituted amino group, a free, etherified or esterified hydroxy or mercapto group or $Z_1$ and $Z_2$ together can represent sulphur or oxygen.

If Y represents hydrogen ($H_2$), $Z_1$ and $Z_2$ will generally be halogen or hydroxy groups. Reagents belonging to this group of substances are for instance: methylene chloride, methylene bromide or methylene diol (= formaldehyde solution in water or an aqueous solvent).

If Y represents oxygen or sulphur, the most suitable moieties for $Z_1$ and $Z_2$ are: halogen, a substituted or unsubstituted amino group, an etherified or esterified, preferably a sulfonylated, hydroxy or mercapto group, or ($Z_1$ and $Z_2$) together a sulphur atom (in combination with Y = sulphur). Suitable reagents of the general formula III belonging to this group of substances are for example: phosgene, thiophosgene, haloformic acid esters such as ethylchloroformate, carbonic acid esters, such as dialkylcarbonate, carbondisulfide, urea or compounds derived from urea, such as thiourea or N,N'-carbonyl-diimidazol.

Preferably methylenehalide or formaldehyde in water is used as the reagent III in the condensation reaction with the diamine II (Q = $H_2$) as the desired final product according to the invention is obtained directly without any additional chemical conversion.

If a reagent III, in which Y represents oxygen or sulphur and/or a compound II, in which Q represents oxygen, is applied as starting material the compound obtained after the condensation must be reduced to the desired final product additionally. For such a reduction any suitable reducing agent can be used, for example metal hydrides such as sodium hydride, lithium-aluminium hydride or diborane. Said reduction can also be performed catalytically by hydrogenation in the presence of a metal or a metal compound.

If $Z_1$ and/or $Z_2$ represent halogen, the condensation reaction should preferably be carried out in alkaline environment, e.g. by adding pyridine or triethylamine to the reaction mixture, in order to remove the hydrohalide formed during the condensation.

The condensation reaction can be performed in any suitable solvent. If methylene halide is used as the reagent (III), an aprotic polar solvent such as dimethylsulfoxide, sulfolane or acetonitril, is preferred. It is also possible, however, to carry out the condensation without the use of an extra solvent; in that case the compound III e.g. methylenechloride or methylenebromide, serves as one of the reaction components and solvent as well. In some cases the condensation reaction may preferably be performed in a melt, for example where urea is used as the reagent III.

The starting substances of formula II can be prepared by any method commonly used for this type of compounds.

For example the compounds II may be obtained by reacting aniline or an aniline derivative (R₁ substituent) with an α-bromophenyl acetic ester, converting the resulting product in an amide by aminolysis of the ester and after that, if desired, reducing the amide in a known manner for example, with LiAlH₄.

With salts of the compounds I according to the invention are meant the pharmaceutically acceptable acid addition salts and quaternary ammonium salts thereof.

The acid addition salts of the compounds according to the invention are obtained in the usual manner by contacting the free base with an organic or inorganic acid such as hydrochloric acid, hydrobromic acid, sulfuric acid, phosphoric acid, acetic acid, fumaric acid, propionic acid, glycollic acid, maleic acid, malonic acid, succinic acid, tartaric acid, citric acid, ascorbic acid, salicylic acid or benzoic acid.

The quaternary ammonium compounds, and particularly the lower (1–4 C) alkyl quaternary ammonium compounds are obtained by reacting the compounds of the general formula I with an alkyl halide, for example methyl iodide or methyl bromide.

From the above general formula I it appears that the compounds according to the invention possess an asymmetric carbon atom. This means that optical antipodes of the general formula I are possible, which also form part of the invention. Said optical antipodes I may be isolated from the racemic mixture I in a conventional manner. It is also possible, of course, to resolve the starting product II into its optical antipodes and to carry out the aforesaid condensation reaction after that, or to resolve a racemic intermediate IV (with Q and/or Y is oxygen or sulphur) and to perform the reduction after that.

The possible substituents at one or both phenyl rings of formula I are preferably already present in the starting product II, but can also be introduced or modified in the compound obtained after the aforesaid condensation and optional reduction. For example a hydroxy may be converted into an alkoxy group, an amino group into halogen, a methoxy group into a hydroxy group, etc.

Moreover an unsubstituted nitrogen atom at position 1 of a compound of formula I (R₃ = H) may be (ar)alkylated or the nitrogen-substituent present may be replaced by another group in a conventional manner. It is also a quite usual procedure to convert a compound I, in which R₃ stands for (ar)alkyl, into a compound I, in which R₃ is hydrogen, for example by reacting with a chloroformic acid ester, followed by hydrolysis.

The (ar)alkylation of a compound I (R₃ is H) may be carried out in a conventional manner by reacting with an (ar)alkyl halide, or by acylating the relevant nitrogen atom and reducing after that the carbonyl group of the resulting N-acyl compound in a conventional manner.

For example the (ar)alkylation is effected by acylating with methylformate, acetic anhydride, propionic acid anhydride, hexanoylchloride, benzoylchloride, phenyl acetylchloride or phenylpropionylchloride and reducing the resulting N-acyl compounds with for example LiAlH₄ or diborane.

The compounds according to the invention can be administered both orally and parenterally, preferably in a daily dosage of between 0.01 and 10 mg per kg body weight. Mixed with suitable auxiliaries the compounds can be compressed into solid dosage units such as pills, tablets and coated tablets. They can also be processed into capsules, mixed with auxiliaries, if desired.

By means of suitable liquids the compounds can be applied as injection preparation in the form of solutions, emulsions or suspensions.

Compounds I, which are to be preferred are those bearing no (r and s = 0) or only one substituent (r and/or s = 1) at the benzene ring(s).

An acyloxy group, mentioned in the definition of R₁ and R₂ is preferably derived from an aliphatic carboxylic acid with 1–6 carbon atoms, such as acetoxy, propionyloxy or butyryloxy, or from a phenylaliphatic carboxylic acid with 7 or 8 carbon atoms, such as benzoyloxy or phenylacetoxy.

An aryl group, mentioned in the definition of R₃ is preferably a phenyl group, such as phenyl, p-chlorophenyl, p-tolyl etc., whereas the aralkyl group is preferably a phenylalkyl group with 7–9 carbon atoms, such as benzyl, phenylethyl and phenylpropyl.

In the examples the following nomenclature and numbering have been used:

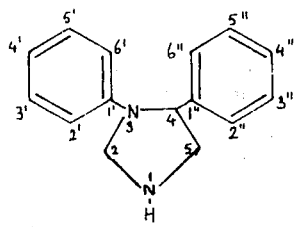

3,4-diphenyl-imidazolidine

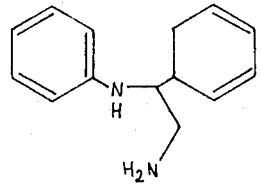

1-phenyl, 1-phenylamino-2-aminoethane or α-anilino-phenylethylamine

EXAMPLE I

Preparation of
1-methyl-3-m.tolyl-4-phenyl-imidazolidine and salts thereof 10 g of the diamino compound 1-phenyl-1-m.tolylamino-2-methylamino-ethane hydrochloride are dissolved in 25% ammonia, after which the solution is extracted with ether. The free base is obtained by evaporating the ether-extracts to dryness. The residue is then dissolved in 100 ml of 96% ethanol, to which 20 ml of 36% formaline has been added. After stirring for 10 minutes the reaction mixture is evaporated in vacuo and the residue dissolved in ether. The ethereal solution is washed with water three times and then evaporated to dryness. The oil obtained is crystallised from petroleumether. Yield: 9.5 g; melting point 73°–75°C.

2 g of the free base obtained is dissolved in ethanol, after which a solution of hydrochloric acid in ethanol (2 N) is added. The crystals obtained are recrystallised from ethanol/ether. Melting point of the HCl-salt: 198°–201°C.

The fumarate is prepared in an identical manner: melting point 169°–170°C.

By reacting the free base with methyliodide, the iodomethylate is obtained; melting point: 186°–187°C.

EXAMPLE II

Preparation of 3-phenyl-4-p-methoxyphenyl-imidazolidine and the corresponding 1-methyl compound 920 mg of the diamino compound 1-p-methoxyphenyl-1-phenylamino-2-amino-ethane are dissolved in 1 ml of 96% ethanol. After that 0.2 ml of formaline (35%) is added to the solution and stirred for 5 minutes.

The reaction mixture is evaporated in vacuo and the residue dissolved in ether. The ether fraction is washed with water (3x) and then evaporated to dryness. Yield: 1.13 g of oil. Rf in toluene:ethanol (4:1) = 0.70 on $SiO_2$.

1.1 g of the compound obtained is alkylated in the usual manner by boiling the compound (in an ampoule) with methylformate for 12 hours and reducing the formylated product with sodium borohydride in ethanol. Obtained in this manner: 800 mg of 1-methyl-3-phenyl-4-p-methoxyphenyl-imidazolidine; melting point 77°–78°C.

EXAMPLE III

The following compounds are prepared in the manner as described in example I, by reacting the corresponding diamine with an aqueous formaldehyde solution.

1-methyl-3(o-chlorophenyl)-4-phenyl-imidazolidine; melting point 75°–77°C, 1-methyl-3-phenyl-4(p-methoxyphenyl)-imidazolidine; melting point 76°–78°C, 1-methyl-3(p-bromophenyl)-4-phenyl-imidazolidine; melting point 70°–71°C, 1-methyl-3(p-chlorophenyl)-4-phenyl-imidazolidine (oil);
Rf in hexane:aceton (65:35) = 0.70 on $SiO_2$, 1-ethyl-3(p-chlorophenyl)-4-phenyl-imidazolidine (oil);
Rf in toluene:ethylacetate (7:3) = 0.6 on $SiO_2$,
Rf in toluene:ethanol (4:1) = 0.7 on $SiO_2$,
Rf in hexane:aceton (65:35) = 0.8 on $SiO_2$, 1-propyl-3(p-chlorophenyl)-4-phenyl-imidazolidine (oil);
Rf in toluene:ethylacetate (7:3) = 0.65, 1-methyl-3,4-diphenyl-imidazolidine.HCl;
melting point 194°–195°C, 1-methyl-3-phenyl-4(p-trifluoromethylphenyl)-imidazolidine (oil):
Rf in toluene:ethylacetate (7:3) = 0.55 on $SiO_2$.

EXAMPLE IV

Preparation of 1-methyl-3-p-tolyl-4-phenyl-imidazolidine

A mixture of 2.5 g of 1-phenyl-1-p-tolylamino-2-methylaminoethane (oil, obtained from the corresponding HCl salt), 10 ml of methylene chloride, 10 ml of dimethylsulfoxide and 2 ml of triethylamine is refluxed for 5 hours. The excess of methylene chloride, triethylamine and the major part of dimethylsulfoxide is then distilled off in vacuo. The remaining liquid is diluted with water and then extracted with ether. The etherial solution is then washed with water, dried and evaporated to dryness.

The residue is a colourless oil: Rf in toluene:ethanol (4:1) = 0.75 on $SiO_2$.

EXAMPLE V

In the manner described in example IV are prepared:

1-methyl-3-m.tolyl-4-phenyl-imidazolidine; melting point 73°–76°C, 1-methyl-3-phenyl-4(p-methoxyphenyl)-imidazolidine; melting point 77°–79°C, 1-methyl-3(o,p-dimethoxyphenyl)-4-phenyl-imidazolidine (oil):
Rf in hexane:aceton (7:3) = 0.45 on $SiO_2$, 1-methyl-3,4-diphenyl-imidazolidine (oil); melting point HCl salt 192°–195°C, 1-methyl-3(p-bromophenyl)-4-phenyl-imidazolidine: melting point 70°–71°C, 1-methyl-3-m.tolyl-4(p-methoxyphenyl)-imidazolidine; melting point 72°–78°C, 1-methyl-3-o.chlorophenyl-4-phenyl-imidazolidine; melting point 75°–77°C, 1-methyl-3-phenyl-4(o.methyl, p-methoxyphenyl)-imidazolidine (oil).

EXAMPLE VI

Preparation of 1-ethyl- and 1-benzyl-3,4-diphenyl-imidazolidine 1.5 g of the free base 3,4-diphenyl-imidazolidine, is acylated in benzene with the aid of acetic anhydride or benzoylchloride and pyridine.

The reaction mixture is poured out into 1 N NaOH and the mixture obtained extracted with ether and evaporated to dryness.

The remaining oil (N-acetyl or N-benzoyl derivative) is dissolved in 10 ml of tetrahydrofuran, after which the solution, while stirring, is added carefully to a suspension of 0.5 g $LiAlH_4$ in 25 ml THF. The mixture is refluxed for 1 hour after which it is cooled down. Then 2 ml of water are slowly added to the reaction mixture, after which the suspension is filtered off, After that the filtrate is evaporated to dryness. Rf of 1-ethyl-3,4-diphenyl-imidazolidine in toluene-ethanol (4:1) = 0.80 on $SiO_2$; melting point HCl salt 190°–195°C, Rf of 1-benzyl-3,4-diphenyl-imidazolidine in toluene:ethylacetate (7:3) = 0.85 on $SiO_2$.

EXAMPLE VII

Preparation of 1-methyl-3-m.tolyl-4-phenyl-imidazolidine.fumarate 2 g Of 1-phenyl-1-m.tolylamino-2-methylaminoethane. HCl is converted into the free base by the method described in example I. The oil obtained is dissolved in carbon-disulfide after which the solution is refluxed for 10 hours. The precipitate formed is isolated by filtration. This residue (1-methyl-2-thio-3-m.tolyl-4-phenyl-imidazolidine) is immediately dissolved in THF, after which 1.5 g $LiAlH_4$ is added to the solution. After refluxing for 3 hours the mixture is cooled down, whereupon 6 ml of water is added dropwise. The mixture is then filtered, the filtrate evaporated to dryness and the residue converted with fumaric acid/ethanol into the fumarate salt. Melting point: 168°–170°C.

EXAMPLE VIII

Preparation of 1-methyl-3-m.tolyl-4-phenyl-imidazolidine.HCl

A. A solution of 1.2 g of thiophosgene in 10 ml of toluene is slowly added at 0°C to a solution of 2.2 g of 1-phenyl-1-m-tolylamino-2-methylamino-ethane in 20 ml of toluene, to which 5 ml of pyridine has been added. The reaction mixture is left to stand for one hour after which 20 ml of water are added. After stirring intensively the water layer is separated from the toluene layer. The toluene phase is washed with water, then with 0.02 M sulphuric acid and finally with water. The toluene solution is then dried. after which the solvent is evaporated in vacuo. The residue obtained in reduced in the same manner as described in example VII. Melting point HCl salt 198°–199°C.

B. The same substance is obtained if thiophosgene is replaced by phosgene, ethylchloroformate, dimethylcarbonate or N,N'-carbonyldiimidazol. As a solvent THF is used.

I claim:

1. A compound of the formula:

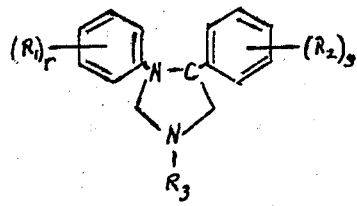

or a pharmaceutically acceptable salt thereof, in which $R_1$ and $R_2$ are selected from the group consisting of halogen, hydroxy, alkyl (1–6 C), alkoxy (1–6 C), and trifluoromethyl, $r$ and $s$ stand for the number 0 – 1, and $R_3$ is alkyl of 1 to 6 carbon atoms.

2. A compound according to claim 1, in which $R_3$ is methyl.

* * * * *